United States Patent [19]
Kuzma

[11] Patent Number: 6,096,059
[45] Date of Patent: Aug. 1, 2000

[54] MICROSURGICAL TOOL

[75] Inventor: Janusz A. Kuzma, Englewood, Colo.

[73] Assignee: Advanced Bionics Corporation, Sylmar, Calif.

[21] Appl. No.: 09/251,761

[22] Filed: Feb. 18, 1999

Related U.S. Application Data

[60] Provisional application No. 60/077,571, Mar. 3, 1998.
[51] Int. Cl.[7] .................................................. A61B 17/28
[52] U.S. Cl. ........................................... 606/208; 606/211
[58] Field of Search ..................................... 606/210, 205, 606/206, 207, 208, 108, 211; 604/161; 128/784

[56] References Cited

U.S. PATENT DOCUMENTS

| | | | |
|---|---|---|---|
| 1,837,277 | 12/1931 | Lund | 606/210 |
| 4,389,912 | 6/1983 | Dallons et al. | 606/210 |
| 4,873,979 | 10/1989 | Hanna | 606/210 |
| 4,898,183 | 2/1990 | Kuzma | 128/784 |
| 5,147,378 | 9/1992 | Markham | 606/210 |
| 5,667,514 | 9/1997 | Heller | 606/108 |
| 5,752,937 | 5/1998 | Otten et al. | 604/161 |
| 5,928,263 | 7/1999 | Hoogeboom | 606/210 |

Primary Examiner—Michael Buiz
Assistant Examiner—Jonathan D. Goldberg
Attorney, Agent, or Firm—Bryant R. Gold

[57] ABSTRACT

A microsurgical tool (8), in the form of forceps, allows access and micro-manipulation into very small confined spaces, such as the cochlea. The microsurgical tool includes an activation body (10) and a working head (20). The activation body is made from a pair of leaf springs (11) joined permanently at one end to a sliding bracket (12) and joined at the other end to a central section (15) with removable screws (13). The central section (15) tapers to an extension (15A) that extends to the working head. A push arm (16) has a first end coupled to the sliding bracket (12) and a second end pivotally joined to the working head (20). The working head (20) is made from a first jaw part (21) attached to the extension (15A), and a second jaw part (22) pivotally connected to the second end of the push arm (16). In operation, pressing the pair of leaf springs together forces the sliding bracket to slide forward and close the first and second jaw parts together, while releasing the pair of leaf springs allows the sliding bracket to slide backward to open the jaw parts.

8 Claims, 4 Drawing Sheets

MICROSURGICAL TOOL

This application claims the benefit of U.S. Provisional Patent Application Ser. No. 60/077,571, filed Mar. 3, 1998.

BACKGROUND OF THE INVENTION

The present invention relates to a surgical tool, and more particularly to a microsurgical tool used in surgery where precision movement and easy access to very small, confined places is critical.

There are a significant number of surgical tools, such as microforceps and microscissors, that are used in surgery where precise movement and easy access to small, confined spaces is needed.

One of the most common and popular designs for such tools is a microscissors of the type shown in FIG. 1. As seen in FIG. 1, a microscissors tool 100 includes a scissor-like activation handle 102 with finger loops 104 and 106. Such a tool 100 may be fitted with a variety of working heads 108, the details of which are shown in FIGS. 1A, 1B, and 1C. In FIG. 1A, for example, upper jaw 110 and lower jaw 111 close on each other like the jaws of an alligator. In FIG. 1B, upper jaw 110' closes against the edge of lower jaw 111'. In FIG. 1C, a first side jaw 112 closes against a second side jaw 113.

Tools of the type shown in FIG. 1, with working heads 108 of the type shown in FIGS. 1A, 1B and 1C, are generally very effective. In some instances, however, the scissor-like construction of the activation part limits the capacity for micro-manipulation which can be achieved more simply by very slight movements of the fingers and wrist. Such problems are particularly noticeable when the tools are used to place electrodes within a cochlea during cochlear implant surgery.

What is needed, therefore, is an improved microsurgical tool that facilitates precise micro-manipulation through simple and slight movements of the fingers and wrist.

SUMMARY OF THE INVENTION

The present invention addresses the above and other needs by providing a microsurgical forceps tool.

The forceps tool provided by the invention includes an activation mechanism and a working head. The working head is adapted for the particular application for which the micro forceps are to be used, e.g., implanting a cochlear electrode within the cochlea of a patient.

The activation mechanism includes two leaf springs joined permanently at one end to a sliding bracket. The other end of the leaf springs is detachably connected to a central section by way of removable screws. The central section tapers into a thinner extension, which is formed at the end into a first jaw part of a jaw made from two parts which close or open against each other.

Located beside the extension is a pusher which is joined to the second jaw parts by a pivotal connection. The other end of the pusher is engaged with an L-shaped slot of the slider.

For use with cochlear implant insertion, the working head is constructed to grasp a cochlear electrode. That is, the jaw parts are bent to an angle of between 90 to 110 degrees with a round opening that is slightly smaller than the diameter of a cochlear electrode.

The method of handling the microsurgical forceps of the present invention is simple and straightforward. The tool is simply held in the hand between the thumb and forefinger. By squeezing the leaf springs, the sliding bracket moves forward. This movement, through the pivotal connection of the jaw, closes the jaw parts against each other. Upon releasing the leaf springs, the sliding bracket is pulled back, opening the jaw parts.

For cleaning and servicing of the microsurgical forceps of the present invention, the two screws holding the leaf springs together at one end are simply removed, and the sliding bracket is disengaged from its pin and slid off to allow access to the remaining structure.

It is a feature of the present invention to provide a microsurgical forceps tool that allows minute manipulations to be achieved through very slight movements of the fingers and wrist.

It is another feature of the invention to provide a surgical tool having jaw parts that open and close in concert with the opening and closing of the surgeons thumb and finger. That is, it is a feature of the invention that the microsurgical forceps tool has a main body part (activation mechanism) that is easily held between the thumb and forefinger of the surgeon, and that the tool's jaws close upon applying a squeezing pressure to the main body part (i.e., by closing the thumb and forefinger together), and that the jaws open upon releasing such pressure (i.e., by opening the thumb and forefinger).

It is a further feature of the invention to provide a surgical tool that is easily disassembled for cleaning and sterilization and easily reassembled for use.

It is yet another feature of the invention to provide microsurgical forceps wherein various types of working heads may be easily attached thereto to facilitate different surgical applications.

BRIEF DESCRIPTION OF THE DRAWINGS

The above and other aspects, features and advantages of the present invention will be more apparent from the following more particular description thereof, presented in conjunction with the following drawings wherein:

FIG. 1A shows one type of working head used with the tool of FIG. 1;

FIG. 1B shows another type of working head used with the tool of FIG. 1;

FIG. 1C shows yet another type of working head commonly used with the tool of FIG. 1;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
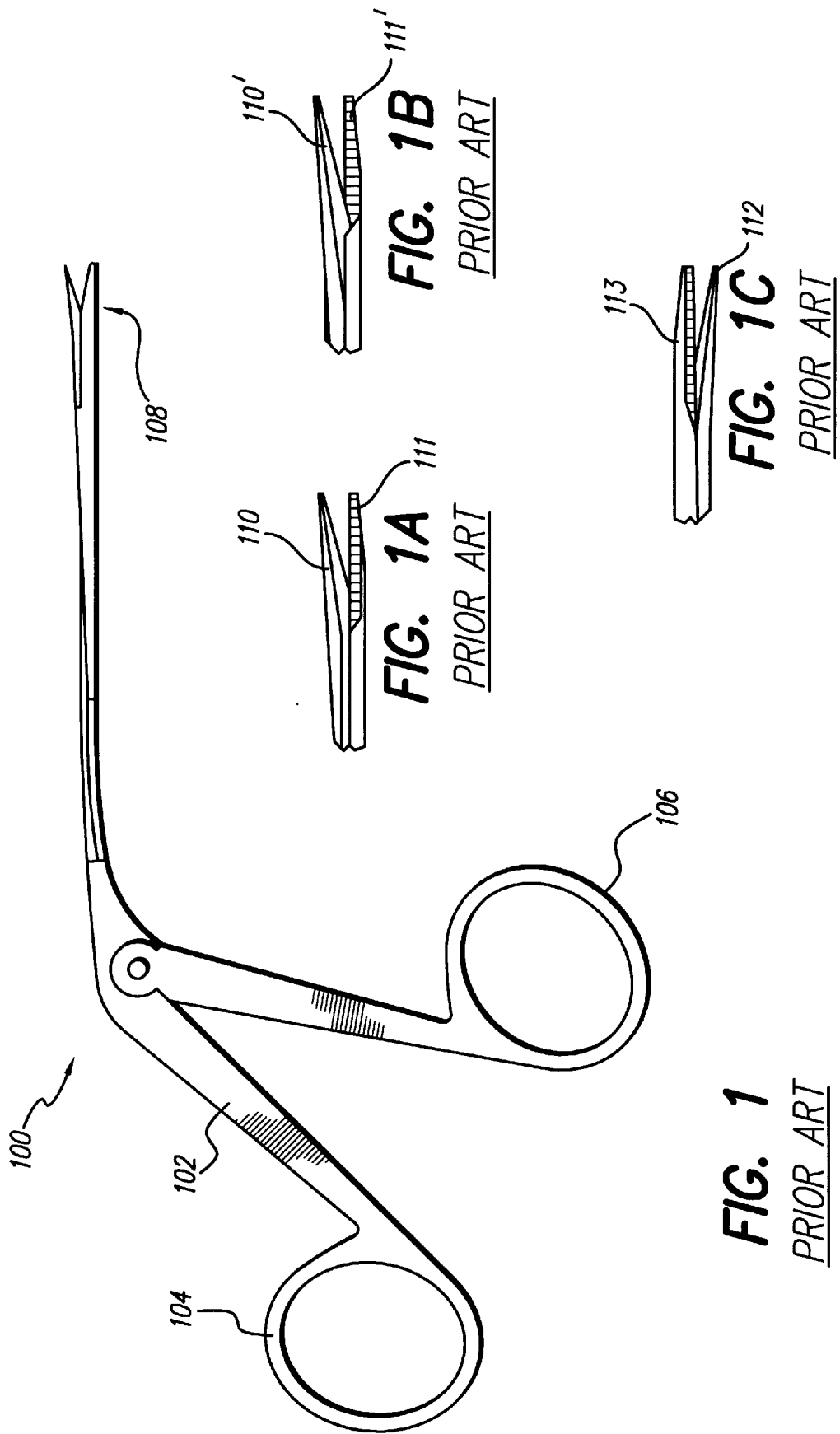
FIG. 1 shows a scissor-type activation mechanism commonly used with prior art surgical tools.

FIG. 1 shows a prior art scissors-type activation type surgical tool 100. The tool 100 includes a main part having a scissors-like activation handle 102 with two finger loops 104 and 106. Various types of working heads 108 may be used with such scissors-like tools. Examples of such working heads are illustrated in FIGS. 1A, 1B and 1C, and have been described previously.

Figure 2:
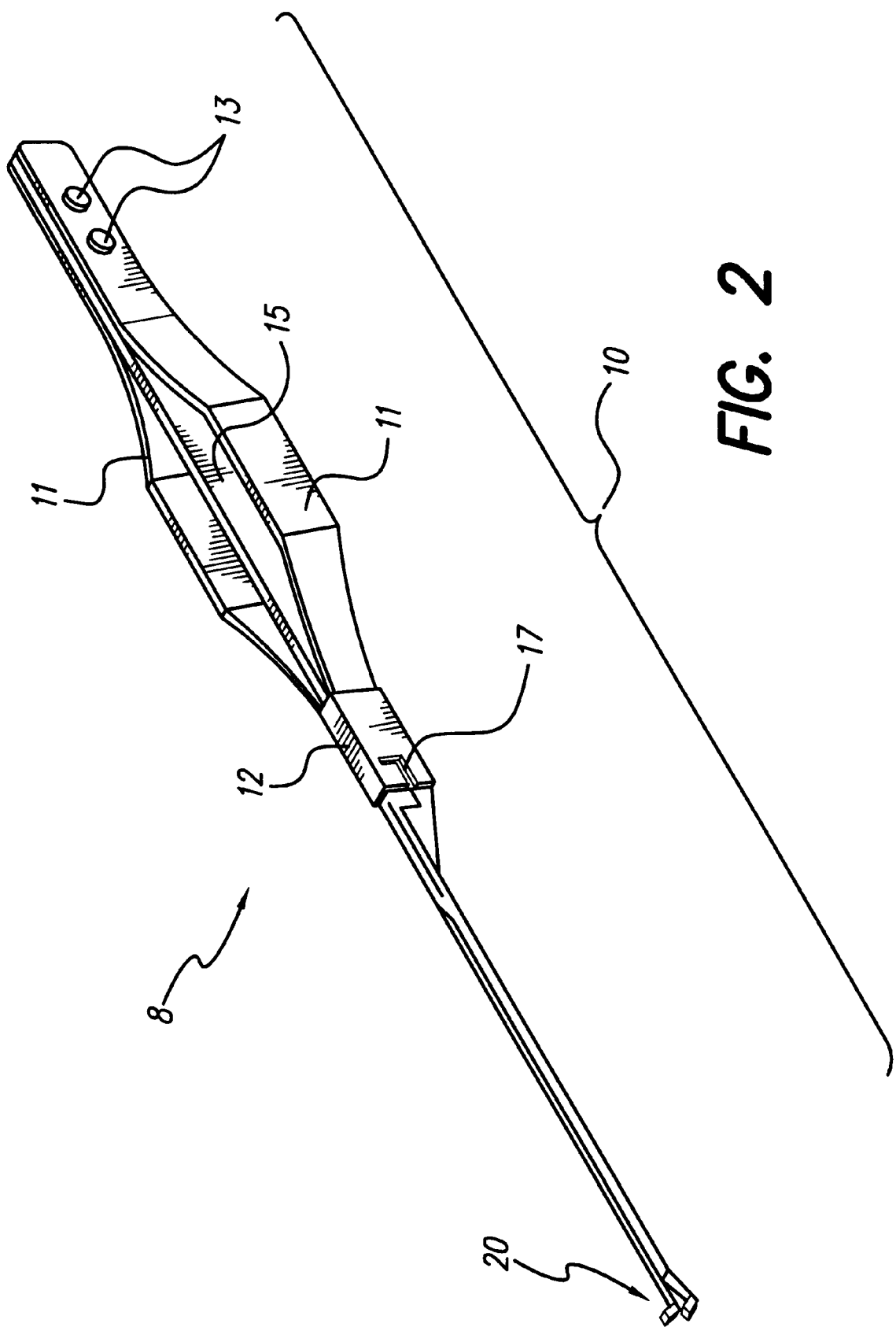
FIG. 2 is a perspective view of a microsurgical forceps tool made in accordance with the present invention.

FIG. 2 is a perspective view of a microsurgical forceps tool 8 made in accordance with the present invention. As seen in FIG. 2, the tool 8 includes an activation mechanism 10 and a working head 20. The activation mechanism 10 includes two leaf springs 11 joined permanently at one end to a sliding bracket 12. The other end of the leaf springs 11 is connected to a central section 15 with two screws 13. The central section 15 tapers into a thinner extension 15A, which is formed at the end into a first jaw part 21 of a jaw 20. The jaw 20, as seen best in FIGS. 4A and 4B, comprises the first part 21 and a second part 22.

Figure 4:
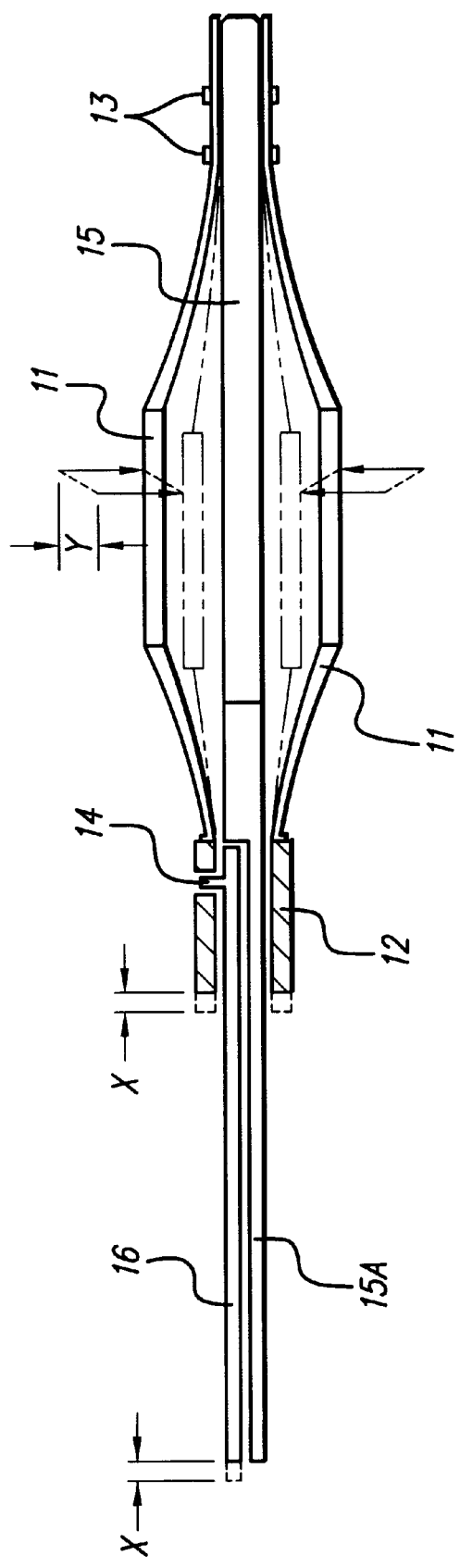
FIG. 4 shows a top view of the microsurgical tool of FIG. 2, and illustrates the manner in which the leaf springs, when compressed, effectuate movement of a sliding bracket, which in turn activates the jaws of the tool to close.

Located beside the extension 15A, and as best seen in FIG. 4, is a push arm 16 (also referred to as a "pusher" 16). The push arm 16 is joined to jaw part 22 by a pivotal connection 23 (FIG. 4A). The other end of the pusher 16 is engaged with an L-shaped slot 17 (FIG. 2) of the sliding bracket 12.

Figure 4B:
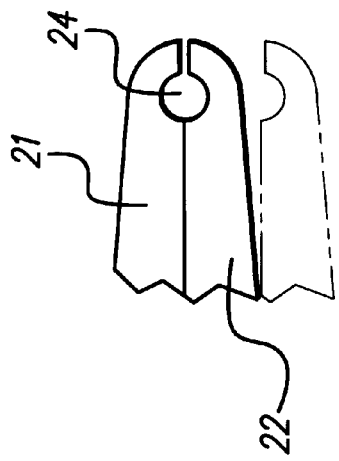
FIG. 4B illustrates a particular type of jaw adapted for grasping a cochlear electrode, or other member having a circular cross section.
Figure 4A:
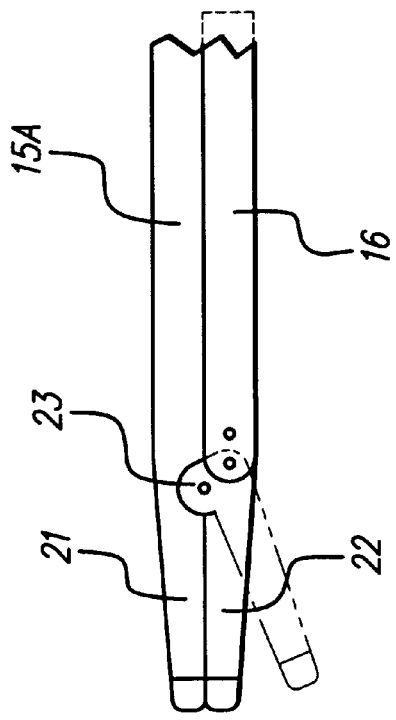
FIG. 4A illustrates the jaws of the tool in their closed and open position.

For use with cochlear implant insertion, the working head 20 is preferably constructed as shown in FIG. 4B. The jaws 21 and 22 are bent or rotated to an angle of between 90 to 110 degrees with a round opening 24 slightly smaller than the diameter of a cochlear electrode. Thus, the cochlear electrode may be readily grasped within the opening 24 and the surgeon, while holding (grasping) the electrode may through his wrist, hand and finger movement insert the electrode into the cochlea to a desired depth. Once inserted, the surgeon then releases the electrode by opening the jaws 21 and 22. In this manner, the tool 8 becomes, as it were, simply an extension (albeit a very fine and micro extension) of the surgeons fingers.

Figure 3:
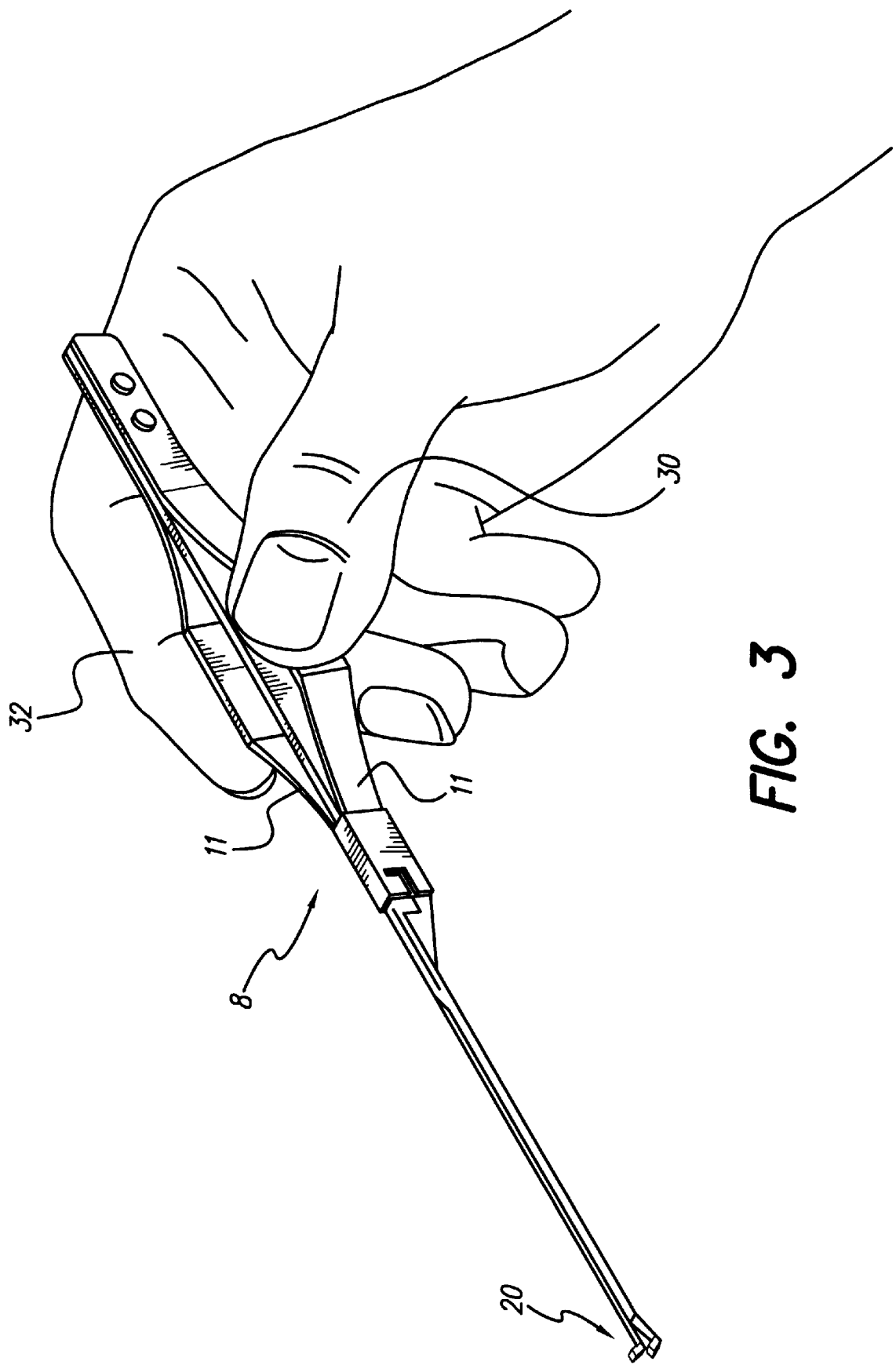
FIG. 3 shows the manner of using the forceps tool of FIG. 2.

The method of handling the microsurgical forceps of the present invention is illustrated in FIG. 3. The tool 8 is held in the hand of a surgeon between the thumb 30 and forefinger 32. By squeezing the thumb and forefinger together, and by thereby squeezing the leaf springs 11 together a distance Y (FIG. 4), the sliding bracket 12 moves forward a distance X (FIG. 4). This movement X, through the pivotal connection 23, closes jaws 21 and 22.

Upon releasing the leaf springs 11, i.e., by separating the thumb and forefinger, the sliding bracket 12 is pulled back, opening jaws 21 and 22.

It is thus seen that the tool 8 advantageously has jaw parts 21 and 22 that open and close in concert with the opening and closing of the surgeon's thumb and finger. That is, the tool 8 has a main body part (activation mechanism 10) that is easily held between the thumb 30 and forefinger 32 of the surgeon. The tool's jaws close upon applying a squeezing pressure to the main body part (i.e., by closing the thumb and forefinger together), and the jaws open upon releasing such pressure (i.e., by opening the thumb and forefinger).

Another important feature of the invention is that the tool 8 is easily cleaned and sterilized. That is, for cleaning and servicing the microforceps 8, the two screws 13 may be removed, and the sliding bracket 12 is disengaged from pin 14 (FIG. 4) and slid off to allow access to the remaining structure.

The tool 8 may be designed with various types of working heads 20, e.g., of the type shown in FIGS. 1A, 1B, 1C, FIG. 4B, or other types of heads, depending upon the particular application for which the tool is to be used.

While the invention herein disclosed has been described by means of specific embodiments and applications thereof, numerous modifications and variations could be made thereto by those skilled in the art without departing from the scope of the invention set forth in the claims.

What is claimed is:

1. Surgical forceps comprising:

an activation body (10); and a working head (20);

the activation body comprising a pair of leaf springs (11) joined permanently at one end to a sliding bracket (12) and joined at the other end to a central section (15) with removable screws (13), the central section (15) tapering to an extension (15A) that extends to the working head;

a push arm (16) having a first end coupled to the sliding bracket (12) and a second end pivotally joined to the working head (20);

the working head (20) comprising a first jaw part (21) attached to the extension (15A), and a second jaw part (22) pivotally connected to the second end of the push arm (16);

wherein pressing the pair of leaf springs together forces the sliding bracket to slide forward and close the first and second jaw parts together, and releasing the pair of leaf springs allows the sliding bracket to slide backward to open the jaw parts of the working head.

2. The surgical forceps of claim 1 wherein the push arm (16) is detachably coupled to the sliding bracket (12), and wherein the removable screws (13), when removed, allow dismantling and cleaning of the forceps.

3. The surgical forceps of claim 2 wherein the first and second jaws (21 and 22) are bent at an angle relative to the extension (15A) and include an opening (24) therein sized for grasping a cochlear electrode, thereby facilitating the insertion of a cochlear electrode.

4. The surgical forceps of claim 2 wherein the first end of the push arm (16) includes a pin (14) adapted for insertion into an L-shaped slot (17) located in the sliding bracket (12).

5. Surgical forceps comprising an activation body and a working head, wherein the activation body comprises:

a central section;

a pair of leaf springs having a first end and a second end, wherein the second end of the pair of leaf springs is detachably joined to the central section with one leaf spring on each side of the central section, and wherein each leaf spring bows away from the center section in the region between the first end and second end, and wherein the first end of the pair of leaf springs makes contact with the central section;

a sliding bracket fitted over the first end of the pair of leaf springs and the central section;

wherein the central section tapers from the location whereat it is joined to the second end of the pair of leaf springs to an extension that extends to a working head beyond the first end of the pair of leaf springs;

a push arm having a first end coupled to the sliding bracket and a second end pivotally joined to the working head;

wherein the working head comprises a first jaw attached to the extension, and a second jaw pivotally connected to the second end of the push arm; and wherein pressing the pair of leaf springs together forces the sliding bracket to slide forward and close the first and second jaws together, and wherein releasing the pair of leaf springs allows the sliding bracket to slide backward to open the jaws of the working head.

6. A microsurgical tool comprising an activation body (10) and a working head (20);

(a) wherein the activation body comprises:

first and second leaf springs (11) joined permanently at one end to a sliding bracket (12) and joined at the other end to a central section (15), wherein the central section (15) resides between the first and second leaf springs and extends past the first and second leaf springs at the point where they are joined to the sliding bracket (12) to the working head (20), a push arm (16) having a first end coupled to the sliding bracket (12) and a second end pivotally joined to the working head (20); and (b) wherein the working head (20) comprises:

first jaw means (21) attached to the extension (15A), and second jaw means (22) pivotally connected to the second end of the push arm (16);

wherein pressing the pair of leaf springs together forces the sliding bracket to slide forward towards the working head and closes the first and second jaw means together, and wherein releasing the pair of leaf springs allows the sliding bracket to slide backward and opens the jaw means.

7. The microsurgical tool of claim 6 wherein the first and second leaf springs have a size and shape that allows the microsurgical tool to be held in the hand of a surgeon between a thumb and forefinger.

8. Surgical forceps comprising:

an activation body (10); and a working head (20);

the activation body comprising a pair of leaf springs (11) joined permanently at one end to a sliding bracket (12) and joined at the other end to a central section (15) with removable screws (13), the central section (15) tapering to an extension (15A) that extends to the working head;

a push arm (16) having a first end coupled to the sliding bracket (12) and a second end pivotally joined to the working head (20);

the working head (20) comprising a first jaw part (21) attached to the extension (15A), and a second jaw part (22) pivotally connected to the second end of the push arm (16);

the first end of the push arm (16) including a pin (14) adapted for insertion into an L-shaped slot (17) located in the sliding bracket (12);

wherein pressing the pair of leaf springs together forces the sliding bracket to slide forward and close the first and second jaw parts together, and releasing the pair of leaf springs allows the sliding bracket to slide backward to open the jaw parts of the working head.

* * * * *